United States Patent [19]

Dorigotti et al.

[11] 4,324,788
[45] Apr. 13, 1982

[54] ALKOXYALKYLIDENHYDRAZINOPRIDA-ZINES AND PROCESS FOR THEIR PREPARATION

[75] Inventors: Luciano Dorigotti, Milan; Giovanni Gaviraghi, Agrate Brianza; Giorgio Pifferi, Milan; Mario Pinza, Corsico; Claudio Semeraro, Bresso, all of Italy

[73] Assignee: I.S.F. S.p.A., Milan, Italy

[21] Appl. No.: 142,457

[22] Filed: Apr. 21, 1980

[30] Foreign Application Priority Data

Apr. 23, 1979 [IT] Italy ............................ 22035 A/79

[51] Int. Cl.³ ................. C07D 237/22; C07D 405/12; A61K 31/50
[52] U.S. Cl. .................................... 424/250; 544/238; 544/239
[58] Field of Search ................ 544/239, 238; 424/250

[56] References Cited

U.S. PATENT DOCUMENTS 3,769,278 10/1973 Pifferi .
4,027,027 5/1977 Iaeggi et al. .................... 544/239
4,082,843 4/1978 Coates et al. .
4,115,575 9/1978 Frei et al. ....................... 544/239

FOREIGN PATENT DOCUMENTS 830158 12/1975 Belgium .
2154245 7/1972 Fed. Rep. of Germany .
2556918 6/1977 Fed. Rep. of Germany .

*Primary Examiner*—Mark L. Berch
*Attorney, Agent, or Firm*—Stevens, Davis, Miller & Mosher

[57] ABSTRACT

There are described new alkoxyalkylidenhydrazinopyridazines having antihypertensive activity having the formula:

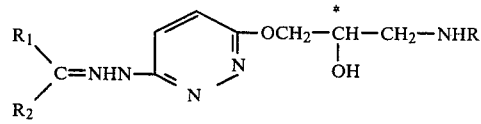

wherein R is alkyl or cycloalkyl having up to 5 carbon atoms, optionally substituted with unsubstituted phenyl, substituted phenyl or cycloalkyl, $R_1$ is hydrogen or alkyl having 1 to 3 carbon atoms and $R_2$ is alkyl having 1 to 3 carbon atoms, a carboxylic group or phenyl and the process for their preparation.

25 Claims, No Drawings

ALKOXYALKYLIDENHYDRAZINOPRIDAZINES AND PROCESS FOR THEIR PREPARATION

The present invention is concerned with new alkoxyalkylidenhydrazinopyridazines having antihypertensive activity and the process for their preparation. More particularly, the following compounds are described having the formula:

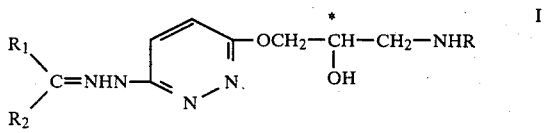

wherein R is alkyl or cycloalkyl having up to 5 carbon atoms, optinally substituted with unsubstituted phenyl, substituted phenyl or cycloalkyl. The preferred substituted phenyl is phenyl having at least one $C_1$–$C_3$ alkoxy substituent or a methylenedioxy group. Among these there may be mentioned paramethoxy, 3,4,5-trimethoxy, 2,3,4-trimethoxy and 3,4-methylenedioxy. The cycloalkyl preferably contains 5 or 6 carbon atoms. Preferred radicals are t.butyl, n.butyl, 2-butyl, isopropyl, cyclopropyl, benzyl, 2-phenyl-ethyl, 3-phenyl-2-propyl, 4-phenyl-2-butyl, 3,4-dimethoxy-phenyl-2-ethyl, 4-cyclohexyl-2-butyl. $R_1$ is hydrogen or alkyl having 1 to 3 carbon atoms and $R_2$ is alkyl having 1 to 3 carbon atoms, a carboxylic group or phenyl.

The presence of the asymmetric carbon atom, indicated by an asterisk in formula I indicates that each compound exists in two optically active forms and may therefore be present separated as the same or in the racemic form.

Compounds of formula I are prepared starting from 3,6-dichloropyridazine which is reacted with isopropylidene glycerol in the presence of a strong base such as for example sodium t.butylate or sodium hydride to obtain 3-chloropyridazine substituted in position 6 (II) with the group 2,2-dimethyl-1,3dioxolane-4-methoxy. Such reaction is carried out at a temperature between 30° and 80° C. in an aprotic non-polar solvent such as for example toluene, benzene and 1,2-dimethoxyethane. Compound II is then treated in a suitable solvent at a temperature from 60° to 90° C. with hydrazine and successively with a carbonyl derivative $R_1COR_2$ where $R_1$ and $R_2$ have the same meanings above indicated, provided that where $R_2$ is a carboxylic group it may be advisable to protect it during the following reaction and removing the protection when required. The solvent of the reaction is a protic solvent preferably an alcohol with a low molecular weight such as ethyl and propyl alcohol. The produced hydrazono derivative III is preferably not separated, but rather the reaction mixture is directly acidified while hot by adding a strong acid, as for example hydrochloric acid or p-toluensulphonic acid. The temperature of the reaction is preferably between 40° and 60° C. The produced diol IV is then treated with an alkyl orthoester $R'_1C(OR'_2)_3$ where $R'_1$ is hydrogen, alkyl having from 1 to 3 carbon atoms or phenyl and $R'_2$ is an alkyl having from 1 to 3 carbon atoms or phenyl in a suitable aprotic solvent such as a toluene, benzene, and xylene at a temperature between 60° and 110° C., and the compound V which separates is successively treated with a silyl derivative such as alkylsilyhalide, the alkyl of which is methyl or ethyl and the halide is chlorine, iodine or bromine.

The reaction with the silyl derivative is carried out in a chlorinated aprotic solvent such as methylene chloride or chloroform at a temperature between 20° and 50° C., and the halogen derivative VI so obtained is successively treated with an amine $NH_2R$, where R is as before indicated, in a protic solvent such as a low molecular weight alcohol in the presence of alkaline hydroxide to give the desired compound I. According to a preferred procedure, the following reactions are illustrated:

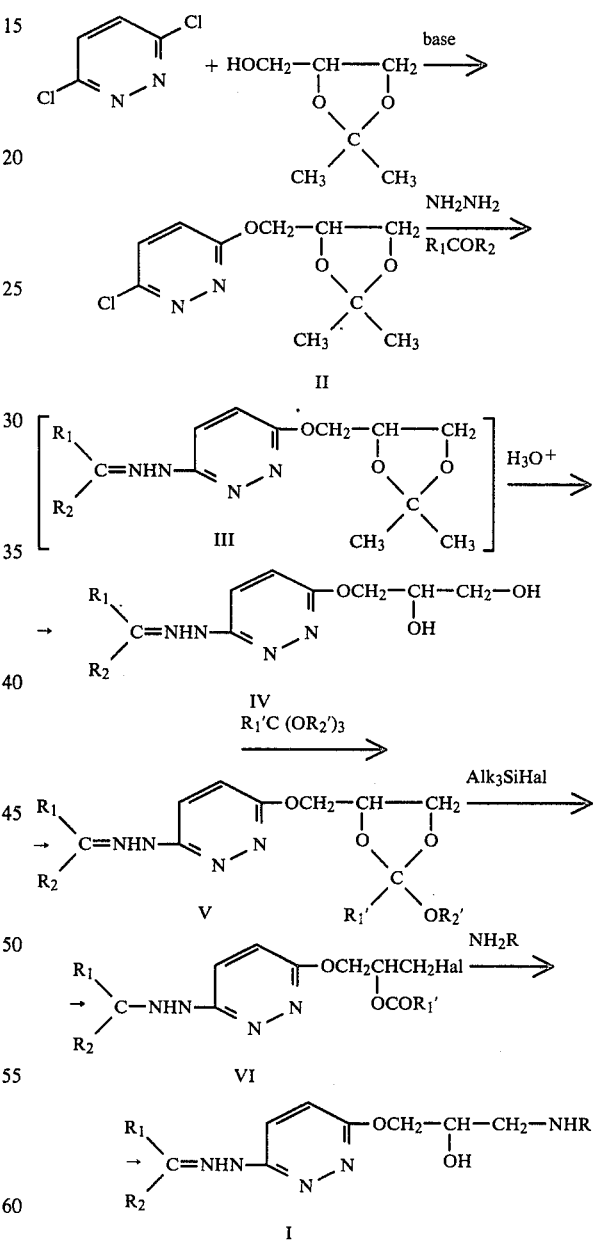

The compounds of the present invention are antihypertensive vasodilator agents practically free from tachycardia at the active dose. Their anti-hypertensive activity is to be referred to a vasal spasmolytic action and such an activity, due to the presence of a certain β-blocking activity, is not accompanied, as it often occurs in almost all the vasodilator drugs, by an increase of the heart rate. The compounds of the invention have been evaluated compared to an anti-hypertensive vasodilator agent (Hydralizine), an anti-hypertensive $\beta$-blocking agent (Propranolol) and an anti-hypertensive $\alpha,\beta$-blocking agent (Labetalol) particularly as regards the following activities:

activity on the arterial pressure and on the heart rate has been studied per os in genetically hypertensive rats according to the method described in Pharm. Research Comm. 8,295,1976. The Table reports $ED_{25}$ graphically evaluated at the moment of the maximum effect dose which represents the quantity of compound capable of determining a drop of the blood pressure (BP) of 25% and an increase of the heart rate (HR) of 25%;

determined evaluating the dose ratio ($DR_4$) which represents the ratio between the effective concentrations ($EC_{50}$) of agonist evaluated in the presence and in the absence of the product under test at the $10^{-4}M$ concentration. $EC_{50}$ represents the quantity of agonist capable of determining at 50% activation of the organ in comparison with a maximal possible activation. The data obtained are reported in the Table. Acute toxicity expressed as Lethal Dose$_{50}$ ($LD_{50}$) has been approximatly evaluated in mice according to the Irwin method [Gordon Res. Conf. Med. Chem. New London, N.H., 3/7–8,133 (1959)]. The invention which comprises also the pharmaceutically acceptable non-toxic salts of the compounds of formula I is illustrated but not limited by the following Examples.

TABLE

| COMPOUND | MOUSE $LD_{50}$ mg/kg i.p. | SHR BP $DE_{25}$ mg/kg/os | RAT HR $DE_{25}$ mg/kg/os | RABBIT AORTA $EC_{50}$ MOLAR | GUINEA-PIG ATRIA $DR_4$ |
|---|---|---|---|---|---|
| 3-(3-t.butyl-amino-2-hydroxy-propoxy)6-iso-propylidenhydra-zinopyridazine dihydrochloride | 500 | 50 | >100 | $27 \times 10^{31\ 4}$ | 78 |
| 3-(3-isopropyl-amino-2-hydroxy-propoxy)6-iso-propylidenhydra-zinopyridazine dihydrocloride | 500 | 350 | >100 | $17 \times 10^{-4}$ | 77 |
| 3-[3-(2-butyl)-amino-2-hydroxy-propoxy]6-iso-propylidenhydra-zinopyridazine dihydrochloride | 300 | 25 | >50 | — | 72 |
| 3-{3-[2-(3,4-dimethoxy-phenyl)ethyl]-amino-2-hydroxy-propoxy}6-iso-propylidenhydra-zinopyridazine dihydrochloride | 300 | 39 | >60 | — | 531 |
| 3-[3-(4-phenyl-2-butyl)amino-2-hydroxy-propoxy]6-iso-propyliden-hydrazino-pyridazine dihydrochloride | 200 | 17 | >40 | — | 80 |
| Hydralazine | 100 | 8.1 | 6.0 | $6.8 \times 10^{-4}$ | 1 |
| Propanolol | 90 | >400 | >100 | $>1 \times 10^{-2}$ | 6500 |
| Labetalol | 300 | 400 | >100 | $>1 \times 10^{-2}$ | 12590 |

> = no increase of the heart rate at the maximal tested dose spasmolytic activity is determined evaluating the direct relaxant effect on the vasal smooth muscle in vitro on strips of rabbit aorta in which spasm was induced by potassium chloride according to the method described in Journ. of Pharm. and Exper. Therapeutics 205,2,441 (1978). The products were added at sequentially cumulative molar doses and their activity indicated as Effective Concentration ($EC_{50}$). $EC_{50}$ represents that concentration of product capable of relaxing 50% the strip of rabbit aorta rendered spasmodic with 30 mM potassium chloride;

$\beta$-blocking activity was determined in vitro on guinea-pig isolated atria stimulated by isoprenaline hydrochloride used as an agonist at sequentially cumulative molar doses. The compounds under test were added at a single dose of $10^{-4}M$ and their $\beta$-blocking activity

EXAMPLE 1

3-(3-t.Butylamino-2-hydroxypropoxy)-6-isopropylidenhydrazinopyridazine dihydrochloride A solution of 31.1 ml of 2,2-dimethyl-4-hydroxymethyl-1,3-dioxolane and 80 ml dimethyoxyethane is added to a suspension of 13.5 g 50% sodium hydride in 120 ml dimethoxyethane while stirring over a one hour period. The resulting mixture is left while stirring for three hours at ambient temperature, whereafter 37.2 g of 3,6-dichloropyridazine dissolved in 100 ml dimethoxyethane are added over a period of one hour. The reaction mixture is heated for two hours at 60° C., left under stirring overnight at ambient temperature, then the solvent is removed, evaporating under vacuo, and the residue is taken up with 400 ml of water and extracted with 1000 ml ethyl ether. It is made anhydrous over sodium sulphate, then dried under vacuum and the residue obtained crystallized from hexane. 55 grams of 3-chloro-6-(2,2-dimethyl-1,3-dioxolane-4-methoxy)-pyridazine melting at 68° C. are obtained (yield 90%).

40 grams of 3-chloro-6-(2,2-dimethyl-1,3-dioxolane-4-methoxy) pyridazine, 200 ml ethyl alcohol and 300 ml hydrazine hydrate are heated to reflux for 5 hours. The solution is dried under vacuum and the residue, taken up with 50 ml methyl alcohol and 500 ml acetone, is kept under stirring overnight at ambient temperature. The residue obtained through evaporation under vacuum is taken up with 100 ml water and adjusted with 20% hydrochloric acid to pH 1. The product obtained is heated at 60° C. for one hour, then cooled to ambient temperature and neutralized by addition of sodium bicarbonate. The mixture is then extracted six times with 50 ml diethyl ether and the aqueous layer is acidified again, with hydrochloric acid, to pH 1 and dried; the residue obtained, crystallized from 500 ml of a mixture ethyl alcohol:acetone (90:10) gives 16 g of 3-(2,3-dihydroxypropoxy)-6-isopropylidenhydrazinopyridazine hydrochloride melting at 187°-189° C. (yield 36%). A mixture of 16.5 g of 3-(2,3-dihydroxypropoxy)-6-isopropylidenhydrazinopyridazine hydrochloride, 100 ml toluene, 9 ml triethylamine and 11.3 ml methyl orthoacetate is heated for three hours at 100° C. After cooling to ambient temperature the reaction mixture is diluted with 100 ml diethyl ether and washed twice with 30 ml water, then the organic layer is made anhydrous over sodium sulphate and evaporated to dryness. The residue, crystallized from benzene-hexane gives 11 g 3-(2-methyl-2-methoxy-dioxolan-4-methoxy)-6-isopropylidenhydrazinopyridazine melting at 119°-121° C. (yield 61.90%).

A mixture of 8.9 g 3-(2-methyl-2-methoxydioxolan-4-methoxy)-6-isopropylidenhydrazinopyridazine, 50 ml methylene chloride and 5.9 ml trimethylsilylchloride is heated for 2 hours at 40° C. It is then cooled and washed with a saturated solution of sodium bicarbonate, made anhydrous over sodium sulphate and dried. The oily residue is purified on a silica gel column and gives 2.2 g 3-(2-acetoxy-3-chloro)-propoxy-6-isopropylidenhydrazinopyridazine melting, after crystallization from hexane, at 94°-96° C. (yield 25%).

A solution of 0.4 g sodium hydroxide in 20 ml methyl alcohol is added to a mixture of 2.4 g 3-(2-acetoxy-3-chloro)-propoxy-6-isopropylidenhydrazinopyridazine, 30 ml methyl alcohol and 20 ml t.butylamine. The mixture is kept under stirring at ambient temperature for 24 hours, dried, and the residue is taken up with 50 ml chloroform, washed three times with 50 ml water and the organic layer is made anhydrous over sodium sulphate and evaporated under vacuo. The residue obtained is taken up with 20 ml ethyl ether and filtered; the solid is dissolved in 10 ml methyl alcohol with hydrogen chloride and adjusted to pH 1. The mixture is dried and the residue, crystallized from isopropyl alcohol gives 1.76 g 3-(3-t.butylamino-2-hydroxypropoxy)6-isopropylidenhydrazinopyridazine dihydrochloride, melting at 238°-241° C. (with decomposition). Yield 60%.

EXAMPLE 2

3-(3-t.Butylamino-2-hydroxypropoxy)6-benzylidenhydrazinopyridazine dihydrochloride A solution formed by 40 g 3-chloro-6-(2,2-dimethyl-1,3-dioxolane-4-methoxy)pyridazine obtained as previously described, 200 ml ethyl alcohol and 300 ml hydrazine hydrate is refluxed for 5 hours, then dried; the residue is taken up with 100 ml methyl alcohol, treated with 13 g potassium carbonate, stirred for 20 minutes and dried. The residue is taken up with 50 ml water and extracted three times with 200 ml chloroform. The organic layer is washed twice with 20 ml water and after evaporation the residue obtained is dissolved in 500 ml methyl alcohol, to which is added 16 ml benzaldehyde and heated for 30 minutes at 50° C. The mixture is dried, 100 ml water are added to the residue, the pH is adjusted to 1 with 20% hydrochloric acid and heated for 1 hour at 60° C. The solvent is then removed by evaporation, the residue neutralized with a saturated solution of sodium bicarbonate and the solid separated by filtration. After crystallization from ethyl alcohol 16 g 3-(2,3-dihydroxypropoxy)-6-benzylidenhydrazinopyridazine are obtained, melting at 213°-214° C. (yield 34.7%).

A mixture of 14.5 g 3-(2,3-dihydroxypropoxy)-6-benzylidenhydrazinopyridazine, 100 ml toluene, 10 ml methyl orthoacetate and 1 g p-toluenesulphonic acid is heated to reflux for 4 hours. After cooling, the solution is diluted with 100 ml methylene chloride and washed with a saturated sodium bicarbonate solution. The organic layer is made anhydrous over sodium sulphate and dried under vacuo. The residue obtained is taken up with diethyl ether and separated by filtration. 14 grams of 3-(2-methyl-2-methoxydioxolane-4-methoxy)-6-benzylidenhydrazinopyridazine melting at 165°-167° C. are obtained. Yield 81%.

A mixture of 12 g 3-(2-methyl-2-methoxydioxolane-4-methoxy)-6-benzylidenhydrazinopyridazine, 100 ml methylene chloride and 12 ml trimethylsilylchloride is heated for 2 hours at 40° C. It is then cooled, washed with saturated sodium bicarbonate solution, made anhydrous over sodium sulphate and dried. The residue taken up with 50 ml diethyl ether and filtered gives 5.6 g 3-(2-acetoxy-3-chloro)propoxy-6-benzylidenhydrazinopyridazine melting at 140°-144° C. (Yield 40%). A solution of 0.4 g sodium hydroxide in 20 ml methyl alcohol is added to a mixture of 2.8 g 3-(2-acetoxy-3-chloro)propoxy-6-benzylidenhydrazinopyridazine, 30 ml methyl alcohol and 20 ml t.butylamine. The mixture is kept under stirring at ambient temperature for 24 hours, then is dried and the residue obtained is taken up with 20 ml chloroform and washed three times with 10 ml water. The organic layer is made anhydrous over sodium sulphate, evaporated to dryness and the residue taken up with 10 ml ethyl ether and filtered gives 1.1 g 3-(3-t.butylamino-2-hydroxypropoxy)6-benzylidenhydrazinopyridazine dihydrochloride melting at 192°-196° C. (with decomposition). Yield 40%.

EXAMPLE 3

3-(3-Isopropylamino-2-hydroxypropoxy)-6-isopropylidenhydrazinopyridazine dihydrochloride Operating in a manner similar to that described above, 3-(2-acetoxy-3-chloro)propoxy-6-isopropylidenhydrazinopyridazine is reacted with isopropylamine to give 3-(3-isopropylamino-2-hydroxypropoxy)-6-isopropylidenhydrazinopyridazine dihydrochloride, melting, after crystallization from ethyl alcohol:acetone, at 218°-220° C. (with decomposition). Yield 40%.

EXAMPLE 4

3-(3-Cyclopropylamino-2-hydroxypropoxy)6-isopropylidenhydrazinopyridazine dihydrochloride Operating in a manner similar to that described above, 3-(2-acetoxy-3-chloro)propoxy-6-isopropylidenhydrazinopyridazine is reacted with cyclopropylamine to give 3-(3-cyclopropylamino-2-hydroxypropoxy)-6-isopropylidenhydrazynopyridazine dihydrochloride, melting, after crystallization from ethyl alcohol:acetone, at 211°-212° C. (with decomposition). Yield 35%.

EXAMPLES 5-11

Operating in a manner similar to that described above, 3-(2-acetoxy-3-chloropropoxy)6-isopropylidenhydrazinopyridazine is reacted with the suitable amine to give:

3-(3-benzylamino-2-hydroxypropoxy)-6-isopropylidenhydrazinopyridazine dihydrochloride, melting at 216° C. (with decomposition)

3-[3-(2-phenylethyl)amino-2-hydroxypropoxy]6-isopropylidenhydrazinopyridazine dihydrochloride, melting at 217°-222° C. (with decomposition)

3-[3-(3-phenyl-2-propyl)amino-2-hydroxypropoxy]6-isopropylidenhydrazinopyridazine dihydrochloride, melting at 204°-207° C. (with decomposition)

3-[3-(4-phenyl-2-butyl)amino-2-hydroxypropoxy]6-isopropylidenhydrazinopyridazine dihydrochloride, melting at 170°-175° C. (with decomposition)

3-{3[2(3,4-dimethoxyphenyl)ethyl]amino-2-hydroxypropoxy}6-isopropylidenhydrazinopyridazine dihydrochloride, melting at 210°-215° C. (with decomposition)

3-[3-(2-butyl)amino-2-hydroxypropoxy]6-isopropylidenhydrazinopyridazine dihydrochloride, melting at 205°-209° C. (with decomposition)

3-[3-(4-cyclohexyl-2-butylamino-2-hydroxypropoxy]-6-isopropylidenhydrazinopyridazine dihydrochloride, melting at 210°-214° C. (with decomposition)

EXAMPLE 12

3-(3-t.Butylamino-2-hydroxypropoxy)6-(1-carboxyethylidenhydrazino)pyridazine dihydrochloride A mixture of 0.6 g 3-(t.butylamino-2-hydroxypropoxy)6-isopropylidenhydrazinopyridazine dihydrochloride, 0.1 g pyruvic acid, 5 ml water and 1 ml glacial acetic acid is heated under stirring at 50° C. for 24 hours. The mixture is evaporated under vacuo to dryness and the residue taken up with isopropyl alcohol and filtered. 0.15 grams of 3-(3-t.butylamino-2-hydroxypropoxy)6-(1-carboxyethylidenhydrazino)pyridazine dihydrochloride are obtained, melting at 187°-192° C. (with decomposition).

What is claimed is:

1. 3-Alkoxy-6-Alkylidenhydrazinopyridazines

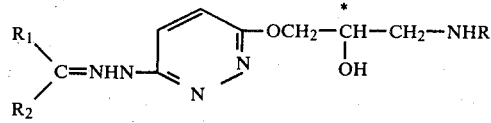

wherein R is alkyl or cycloalkyl having up to 5 carbon atoms, optionally substituted with one of the following: unsubstituted phenyl, phenyl substituted by one, two or three $C_1$-$C_3$ alkoxy substituents or a methylene-dioxy group, or cycloalkyl, $R_1$ is hydrogen or alkyl having from 1 to 3 carbon atoms and $R_2$ is alkyl having from 1 to 3 carbon atoms, carboxyl or phenyl in the form of optically active isomers or a mixture of same and the corresponding pharmaceutically acceptable nontoxic acid addition salts.

2. 3-[3-(4-Phenyl-2-butyl)amino-2-hydroxypropoxy]6-isopropylidenhydrazinopyridazine dihydrochloride.
3. The compound of claim 1 wherein R is alkyl.
4. The compound of claim 1 wherein R is cycloalkyl.
5. The compound of claim 1 wherein R is phenyl-alkyl.
6. The compound of claim 1 wherein R is substituted phenyl-alkyl.
7. The compound of claim 1 wherein R is benzyl.
8. The compound of claim 1 wherein R is phenyl-ethyl.
9. The compound of claim 1 wherein R is phenyl-propyl.
10. The compound of claim 1 wherein R is phenyl-butyl.
11. The compound of claim 2 wherein R is alkyl substituted with a phenyl having one, two or three $C_{1-3}$ alkoxy groups.
12. The compound of claim 1 wherein R is paramethoxy-phenyl-alkyl.
13. The compound of claim 1 wherein R is 3,4-dimethoxy-phenyl-alkyl.
14. The compound of claim 1 wherein R is trimethoxy-phenyl-alkyl.
15. The compound of claim 1 wherein R is methylenedioxy-phenyl-alkyl.
16. The compound of claim 1 wherein $R_1$ is hydrogen.
17. The compound of claim 1 wherein $R_1$ is $C_{1-3}$ alkyl.
18. The compound of claim 1 wherein $R_2$ is $C_{1-3}$ alkyl.
19. The compound of claim 1 wherein $R_2$ is carboxyl.
20. The compound of claim 1 wherein $R_2$ is phenyl.
21. 3-(3-t.Butylamino-2-hydroxypropoxy)6-isopropylidenhydrazinopyridazine dihydrochloride.
22. 3-(3-Isopropylamino-2-hydroxypropoxy)6-isopropylidenhydrazinopyridazine dihydrochloride.
23. 3-[3-(2-Butyl)amino-2-hydroxypropoxy]6-isopropylidenhydrazinopyridazine dihydrochloride.
24. 3-{3[2(3,4-Dimethoxyphenyl)ethyl]amino-2-hydroxypropoxy}6-isopropylidenhydrazinopyridazine dihydrochloride.
25. A pharmaceutical composition containing an antihypertensively effective amount of a compound according to claim 1 in admixture with a pharmaceutically acceptable diluent.

UNITED STATES PATENT AND TRADEMARK OFFICE
CERTIFICATE OF CORRECTION

PATENT NO. : 4,324,788
DATED : April 13, 1982
INVENTOR(S) : Luciano DORIGOTTI et al It is certified that error appears in the above—identified patent and that said Letters Patent is hereby corrected as shown below:

In the Table bridging columns 3 and 4, under the fourth column heading entitled

" RABBIT AORTA $EC_{50}$ MOLAR "  change the first listed compound from "$27 \times 10^{314}$" to -- $27 \times 10^{-4}$ --

Signed and Sealed this

Third Day of August 1982

[SEAL]

Attest:

*Attesting Officer*

GERALD J. MOSSINGHOFF
*Commissioner of Patents and Trademarks*